(12) United States Patent
Sagata et al.

(10) Patent No.: US 8,734,966 B2
(45) Date of Patent: *May 27, 2014

(54) FLUOROPOLYETHER COMPOUND, LUBRICANT AND MAGNETIC DISK EACH CONTAINING THE SAME

(71) Applicant: MORESCO Corporation, Hyogo (JP)

(72) Inventors: Ryosuke Sagata, Hyogo (JP); Tsuyoshi Shimizu, Hyogo (JP); Tomomi Hatta, Hyogo (JP); Nagayoshi Kobayashi, Hyogo (JP)

(73) Assignee: Moresco Corporation, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/765,838

(22) Filed: Feb. 13, 2013

(65) Prior Publication Data

US 2013/0209837 A1    Aug. 15, 2013

(30) Foreign Application Priority Data

Feb. 13, 2012 (JP) ................................. 2012-028593

(51) Int. Cl.
*G11B 5/66* (2006.01)
(52) U.S. Cl.
USPC .................. 428/835.8; 508/582; 570/127
(58) Field of Classification Search
None
See application file for complete search history.

(56) References Cited

U.S. PATENT DOCUMENTS

| 6,608,009 B2 | 8/2003 | Akada et al. |
| 7,670,695 B2 | 3/2010 | Wakabayashi et al. |
| 2012/0315504 A1* | 12/2012 | Shimizu et al. ............... 428/800 |

OTHER PUBLICATIONS

English Machine translation of JP 2010-086598, Hoya Corp, Japan, Apr. 15, 2010.*
N. Tagawa et al., "Spreading of Novel Cyclotriphosphazine-Terminated PFPE Films on Carbon Surfaces", Journal of Tribology, vol. 126, Oct. 2004, pp. 751-754.
Kasai et al., "Disk Lubricant Additives, A20H and C2: Characteristics and Chemistry in the Disk Environment", Tribology Letters, vol. 31, 2008, pp. 25-35.

* cited by examiner

*Primary Examiner* — Holly Rickman
(74) *Attorney, Agent, or Firm* — Wenderoth, Lind & Ponack, L.L.P

(57) ABSTRACT

A compound of the formula (1), lubricant containing the compound and magnetic disk $$R^1—C_6H_4O—CH_2CH(OH)CH_2OCH_2—R^2—CH_2—O—R^3 \quad (1)$$

wherein $R^1$ is hydrogen, alkoxyl having 1 to 4 carbon atoms, amino or amido, $R^2$ is $—CF_2O(CF_2CF_2O)_x(CF_2O)_yCF_2—$, $—CF_2CF_2O(CF_2CF_2CF_2O)_z—CF_2CF_2—$ or $—CF_2CF_2CF_2O(CF_2CF_2CF_2CF_2O)_nCF_2CF_2CF_2—$, x and y are each an integer of 0 to 15, z is an integer of 1 to 15, n is an integer of 0 to 4, $R^3$ is $—CH_2CH(OH)CH_2OH$, $—CH_2CH(OH)CH_2OCH_2CH(OH)CH_2OH$ or $—(CH_2)_mOH$, m is an integer of 2 to 6.

6 Claims, 1 Drawing Sheet

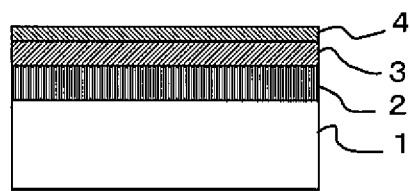

FLUOROPOLYETHER COMPOUND, LUBRICANT AND MAGNETIC DISK EACH CONTAINING THE SAME

TECHNICAL FIELD

The present invention relates to fluoropolyether compounds having an aromatic group and hydroxyl, lubricants containing the compound and magnetic disks having the lubricant applied thereto.

BACKGROUND ART

With an increase in the recording density of magnetic disks, the distance between the magnetic disk serving as a recording medium and the head for use in recording of information or playback has become almost nil close to contact therebetween. The magnetic disk is provided over the surface thereof with a carbon protective film or lubricant film for the purpose of diminishing abrasion due to the contact or sliding of the head thereon or preventing contamination of the disk surface.

The carbon protective film is produced generally by the sputtering process or CVD process. The disk surface is protected with the two films, i.e., the carbon protective film and the lubricant film thereover.

The lubricants generally in use are fluoropolyethers having functional groups. Examples of functional groups are hydroxyl, amino and cyclophosphazene groups. Particularly, lubricants having a phosphazene group are materials having high resistance to decomposition and known as materials for giving high durability to magnetic disks (for example, Patent Literature 1, 2).

The cyclophosphazene group takes the molecular structure of 6-membered ring comprised of three phosphorus atoms and three nitrogen atoms as a main skeleton, and two substituents lengthening up and down of the 6-membered ring from each phosphorus atom (for example, Nonpatent Literature 1). Although the lubricant film on a magnetic disk is required to be thin more and more under the environment wherein the magnetic head is levitated at a low level for a recent rapidly increasing ever-higher recording density, it is difficult to reduce the bulk of molecules of the cyclophosphazene compound.

Patent Literature 1: JP Patent No. 4137447
Patent Literature 2: JP Patent No. 4570622
Nonpatent Literature 1: Tribology letters, 2008, Vol. 31, p 25-35

An object of the present invention is to provide a compound having a reduced bulk of molecules while maintaining excellent resistance to decomposition similar to that shown by phosphazene compound, lubricants comprising the compound, and magnetic disks.

SUMMARY OF THE INVENTION

The present invention provides the following.
1. A compound of the formula (1)

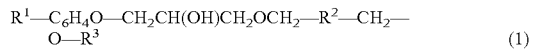

(1)

wherein $R^1$ is hydrogen, alkoxyl having 1 to 4 carbon atoms, amino or amido, $R^2$ is $-CF_2O(CF_2CF_2O)_x(CF_2O)_yCF_2-$, $-CF_2CF_2O(CF_2CF_2CF_2O)_zCF_2CF_2-$ or $-CF_2CF_2CF_2O(CF_2CF_2CF_2CF_2O)_nCF_2CF_2CF_2-$, x and y are each an integer of 0 to 15, z is an integer of 1 to 15, n is an integer of 0 to 4, $R^3$ is $-CH_2CH(OH)CH_2OH$, $-CH_2CH(OH)CH_2OCH_2CH(OH)CH_2OH$ or $-(CH_2)_mOH$, m is an integer of 2 to 6.

2. A lubricant containing a compound of the formula (1).
3. A magnetic disk comprising at least a recording layer and a protective layer formed over a substrate, and a lubricating layer formed over the resulting surface, the lubricating layer containing a compound of the formula (1).

EFFECT OF THE INVENTION

The fluoropolyether compounds of the invention having an aromatic group and hydroxyl are lubricants which solve the two problems of a reduction in mono-layer thickness and resistance to decomposition at the same time. The magnetic disk having the compound of the invention applied thereto enables a reduction in the spacing between the head and the disk, further exhibiting high durability when the head is brought into contact with or slidingly moved on the disk.

EMBODIMENT OF PRACTICING THE INVENTION

Process for Preparing the Lubricant

The lubricant of the formula (1) according to the invention is obtained by reacting, for example, a straight-chain fluoropolyether (a) having a hydroxyl at one terminal and a hydroxyalkyl group at the other terminal with a phenoxy compound having an epoxy group. Stated more specifically, the compound is prepared by the following process.

(1) Synthesis of Straight-Chain Fluoropolyether (a) Having a Hydroxyl at One Terminal and a Hydroxyalkyl Group at the Other Terminal.

A straight-chain fluoropolyether (b) having a hydroxyl at opposite terminals is reacted with a compound (c) reactive with a hydroxyl to produce a hydroxyalkyl group. The reaction temperature is 20 to 90° C., preferably 60 to 80° C. The reaction time is 5 to 20 hours, preferably 10 to 15 hours. The compound (c) is used preferably in an amount of 0.5 to 1.5 equivalents relative to the fluoropolyether (b). A reaction promoting agent may be used. The reaction mixture is thereafter purified, for example, by column chromatography to obtain a straight-chain fluoropolyether (a) having a hydroxyl at one terminal and a hydroxyalkyl group at the other terminal. The reaction may be conducted in a solvent. As a solvent are used, for example, t-butanol, dimethyl formamide, 1,4-dioxane, dimethyl sulfoxide and dimethyl acetamide. Examples of the reaction promoting agents are sodium, potassium t-butoxide and sodium hydride.

The fluoropolyether (b) having hydroxyl at opposite terminals can be, for example, a compound of the formula

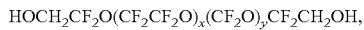

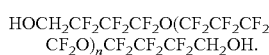

The fluoropolyether is 500 to 2000, preferably 800 to 1500, in number average molecular weight. The number average molecular weight mentioned is a value measured by $^{19}F$-NMR using JNM-ECX400, product of JEOL Ltd. For NMR measurement, the sample itself was used without dilution with a solvent. As a reference for chemical shift, a known peak was used which is a portion of fluoropolyether skeleton structure. x and y are each a real number of 0 to 15, preferably 0 to 10, and when x and y are each a real number of 0 to 10, molecular chain is more flat and preferable. z is a real number of 1 to 15, preferably 1 to 10, and when z is a real number of 1 to 10, molecular chain is more flat and preferable. n is a real number of 0 to 4.

The fluoropolyether (b) is a compound having a molecular weight distribution. The molecular weight distribution (PD), which is weight average molecular weight/number average molecular weight, is 1.0 to 1.5, preferably 1.0 to 1.3, and more preferably 1.0 to 1.1. The molecular weight distribution is a characteristic value obtained by using HPLC-8220GPC, product of Tosoh Co., Ltd., column (PLgel Mixed E), product of Polymer Laboratories, eluent which is HCFC-type alternative CFC and a non-functional perfluoropolyether serving as a reference material.

Examples of compounds (c) reactive with hydroxyl for forming a hydroxyalkyl group are a compound having an epoxy group and haloalkyl alcohol of the formula $X(CH_2)_mOH$, X is a halogen atom, m is a real number of 2 to 8.

Examples of compounds (c) are glycidol, propylene oxide, glycidyl methyl ether, isobutylene oxide, 2-chloroethanol, 3-chloropropanol, 4-chlorobutanol, 5-chloropentanol, 6-chlorohexanol, 7-chloroheptanol, 8-chlorooctanol, 2-bromoethanol, 3-bromopropanol, 4-bromobutanol, 5-bromopentanol, 6-bromohexanol, 7-bromoheptanol, 8-bromooctanol, 2-iodoethanol, 3-iodopropanol, 4-iodobutanol, 5-iodopentanol, 6-iodohexanol, 7-iodoheptanol and 8-iodooctanol.

For example, $HOCH_2CF_2O(CF_2CF_2O)_x(CF_2O)_yCF_2CH_2OH$ is used as compound (b), and glycidol is used as compound (c). The reaction between these two compounds produces $HOCH_2CH(OH)CH_2OCH_2CF_2O(CF_2CF_2O)_x(CF_2O)_yCF_2CH_2OH$ as compound (a).

Further in the case where 2-chloroethanol is used as compound (c), the compound (a) produced is $HOCH_2CH_2OCH_2CF_2O(CF_2CF_2O)_x(CF_2O)_yCF_2CH_2OH$.

(2) Synthesis of Lubricant of the Invention

The fluoropolyether (a) having a hydroxyl at one terminal and a hydroxyalkyl group at the other terminal obtained above is reacted with a phenoxy compound (A) having an epoxy group in the presence of a catalyst. The reaction temperature is 20 to 90° C., preferably 60 to 80° C. The reaction time is 5 to 20 hours, preferably 10 to 15 hours. It is desirable to use the compound (A) in an amount of 1.0 to 2.0 equivalents and the catalyst in an amount of 0.05 to 0.1 equivalent, relative to the compound (a). The catalysts to be used are alkali compounds such as sodium tert-butoxide and potassium tert-butoxide. The reaction may be conducted in a solvent. Examples of solvents to be used are tert-butanol, toluene and xylene. The reaction mixture is thereafter washed, for example, with water and dewatered, whereby a compound (1) of the invention is obtained.

Examples of phenoxy compound (A) having an epoxy group is shown below. $R^1$ is hydrogen, alkoxyl having 1 to 4 carbon atoms, amino or amido group.

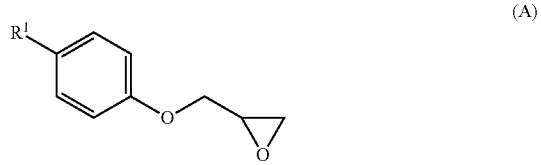

(A)

Examples of phenoxy compound (A) are glycidyl phenyl ether, glycidyl 4-methoxyphenyl ether, glycidyl 4-ethoxyphenyl ether, glycidyl 4-propoxyphenyl ether and glycidyl 4-butoxyphenyl ether.

Further, those wherein $R^1$ is alkoxyl having 1 to 4 carbon atoms, amino or amido group are also usable. Examples thereof are glycidyl 4-methylphenyl ether, glycidyl 4-ethylphenyl ether, glycidyl 4-propylphenyl ether, glycidyl 4-butylphenyl ether, glycidyl 4-aminophenyl ether, glycidyl 4-methylaminophenyl ether, glycidyl 4-dimethylaminophenyl ether, glycidyl 4-ethylaminophenyl ether, glycidyl 4-diethylaminophenyl ether, glycidyl 4-acetamidophenyl ether and glycidyl 4-propionamidophenyl ether.

The compound of the present invention is applied to the magnetic disk surface preferably by diluting the compound with a solvent and coating the disk surface with the diluted compound. Examples of useful solvents are PF-5060, PF-5080, HFE-7100 and HFE-7200 manufactured by 3M, Vertrel-XF, product of DuPont, etc. The concentration of the compound as diluted is up to 1 wt. %, preferably 0.001 to 0.1 wt. %.

While the compound of the invention is usable singly, the compound can be used also as mixed in a desired ratio with another material, such as Fomblin Zdol, Ztetraol, Zdol TX, AM manufactured by Solvay Solexis, Demnum manufactured by Daikin Industries, Ltd. and Krytox manufactured by DuPont.

The compound of the present invention enables the head to be spaced by a small distance from the magnetic disk inside magnetic disk devices and is useful as a lubricant for giving improved durability under a sliding condition. The compound of the invention is characterized by the interaction of the hydroxyl with the polar site present in the carbon protective film and by the interaction of the aromatic group with carbon unsaturated bonds present in the carbon protective film. Accordingly, the compound is usable as a surface protective film for magnetic heads, photomagnetic recording devices, magnetic tapes, plastics and like organic materials having a carbon protective film, and also as a surface protective film for inorganic materials such as glass and metal.

FIG. 1 shows a sectional view schematically showing the magnetic disk of the invention. The magnetic disk of the invention comprises a substrate 1, at least one recording layer 2 formed on the substrate 1, a protective layer 3 on the recording layer 2 and a lubricant layer 4 formed thereon, as an outermost layer, which contains the compound of the invention. The substrate is composed of aluminum alloy, glass and like ceramics, polycarbonate or the like.

The recording layer of the magnetic disk, i.e., the magnetic layer is composed of mainly elements capable of forming ferromagnetic bodies, such as iron, cobalt or nickel, alloy or oxide containing chromium, platinum or tantalum in addition to such elements. These materials are applied by, e.g., a plating method or a sputtering method. The protective layer is formed of carbon, SiC, $SiO_2$ or the like. The layer is formed by a sputtering method or CVD method.

Lubricant layers presently available are up to 20 Å in thickness, so that when a lubricant having a viscosity of higher than about 100 mPa·s at 20° C. is applied as it is, the resulting film is likely to have an excessively large thickness. Accordingly the lubricant for use in coating is used as dissolved in a solvent. When the compound of the present invention is applied as dissolved in a solvent, the film thickness to be obtained is easy to control in the case where the present compound serves singly as a lubricant and also in the case where the compound is used as mixed with other lubricant. The concentration varies with the method and conditions of application, mixing ratio, etc. The lubricant film of the present invention is preferably 5 to 15 Å in thickness.

In order to assure the lubricant of improved adhesion to the ground layer, the lubricant applied can be subjected to heat treatment or ultraviolet treatment. The heat treatment is conducted at 60 to 160° C., preferably at 80 to 160° C. The ultraviolet treatment is conducted using ultraviolet rays of 185 nm and 254 nm in main wavelength.

The magnetic disk of the invention can be applied to a magnetic disk apparatus which can accommodate the disk and which is provided with a magnetic disk drive including a head for recording, reproducing and erasing information and a motor for rotating the disk; and with a control system for controlling the drive.

The magnetic disk of the invention and the magnetic disk apparatus produced using the magnetic disk thereof can be applied for the following: electronic computers, and outer memories for word processors; and can be also applied in navigation systems, games, cellular phone, PHS (personal handyphone system) and like instruments and machines and inner and outer memories for prevention of crimes in buildings, and for management/control systems of power plants.

BRIEF DESCRIPTION OF THE DRAWING

FIG. 1 is a section view showing the structure of the magnetic disk of the invention.

EXAMPLES

The invention will be described in more detail with reference to the following examples to which, however, the invention is not limited.

Example 1

Preparation of $C_6H_5O$—$CH_2CH(OH)$ $CH_2OCH_2CF_2O$—$(CF_2CF_2O)_x(CF_2O)_yCF_2CH_2$—$OCH_2CH(OH)CH_2OH$ (Compound 1)

t-Butanol (41 g), 95 g of a fluoropolyether of the formula HO—$CH_2CF_2O(CF_2CF_2O)_x(CF_2O)_yCF_2CH_2$—OH which is 1305 in number average molecular weight and 1.25 in molecular weight distribution, potassium t-butoxide (0.8 g) and glycidol (8 g) were stirred at 70° C. in an argon atmosphere for 14 hours. The mixture was thereafter washed with water, dewatered and purified by silica gel chromatography, affording 95 g of perfluoropolyether (average molecular weight: 1379) having one hydroxyl group at one terminal and two hydroxyl groups at the other terminal. This compound (95 g) was dissolved in a t-butanol (43 g), potassium t-butoxide (0.4 g) and glycidyl phenyl ether (15 g) were added to the solution, and the mixture was stirred at 70° C. for 14 hours. The mixture was thereafter washed with water, dewatered and purified by distillation, affording 65 g of Compound 1.

Compound 1 was a colorless transparent liquid and 1.75 g/cm³ in density at 20° C. Compound 1 was identified by NMR with the result shown.

$^{19}$F-NMR (solvent: none, reference material: $OCF_2CF_2CF_2CF_2O$ in the obtained product being taken as −125.8 ppm):
δ=−52.1 ppm, −53.7 ppm, −55.4 ppm [12F, —$OCF_2O$—],
δ=−89.1 ppm, −90.7 ppm [24F, —$OCF_2CF_2O$—],
δ=−77.9 ppm, −80.0 ppm [4F, —$OCF_2CH_2OCH_2CH(OH)CH_2$—O—$C_6H_5$, —$OCF_2CH_2OCH_2CH(OH)CH_2OH$],
x=6.1, y=6.4

$^1$H—NMR (solvent: none, reference material: $D_2O$)
δ=3.2~3.8 ppm [17H, $C_6H_5O$—$CH_2CH(OH)CH_2OCH_2$—$CF_2O(CF_2CF_2O)_x(CF_2O)_yCF_2CH_2$—O—$CH_2CH(OH)CH_2OH$]
δ=6.1 ppm, 6.7 ppm [5H, —$OCF_2CH_2OCH_2CH(OH)CH_2$—$C_6H_5$]

Example 2

Preparation of $C_6H_5O$—$CH_2CH(OH)CH_2O$—$CH_2CF_2CF_2O$—$(CF_2CF_2CF_2O)_zCF_2CF_2CH_2$—O—$CH_2CH(OH)CH_2OH$ (Compound 2)

The reaction was conducted in the same manner as in Example 1 except that a fluoropolyether of the formula HO—$CH_2CF_2CF_2O(CF_2CF_2CF_2O)_zCF_2CF_2$—$CH_2$—OH is used in place of the fluoropolyether of the formula HO—$CH_2CF_2O(CF_2CF_2O)_x(CF_2O)_y$—$CF_2CH_2$—OH used in Example 1, affording 61 g of Compound 2.

Compound 2 was a colorless transparent liquid and 1.69 g/cm³ in density at 20° C. Compound 2 was identified by NMR with the result shown.

$^{19}$F-NMR (solvent: none, reference material: $OCF_2CF_2CF_2O$ in the obtained product being taken as −129.7 ppm)
δ=−129.7 ppm [12F, —$OCF_2CF_2CF_2O$—],
δ=−83.7 [24F, —$OCF_2CF_2CF_2O$—],
δ=−124.2 ppm [4F, —$OCF_2CF_2CH_2OCH_2CH(OH)CH_2$—O—$C_6H_5$, —$OCF_2CF_2CH_2OCH_2CH(OH)CH_2OH$],
δ=−86.5 ppm [4F, —$OCF_2CF_2CH_2OCH_2CH(OH)CH_2$—O—$C_6H_5$, —$OCF_2CF_2CH_2OCH_2CH(OH)CH_2OH$]
z=6.3

$^1$H—NMR (solvent: none, reference material: $D_2O$)
δ=3.2~3.8 ppm [16H, $C_6H_5O$—$CH_2CH(OH)CH_2O$—$CH_2CF_2CF_2O(CF_2CF_2CF_2O)_zCF_2CF_2CH_2$—O—$CH_2CH(OH)CH_2OH$]
δ=6.1 ppm, 6.7 ppm [5H, —$OCF_2CF_2CH_2OCH_2CH(OH)CH_2$—$C_6H_5$]

Example 3

Preparation of $C_6H_5O$—$CH_2CH(OH)CH_2O$—$CH_2CF_2CF_2CF_2O$—$(CF_2CF_2CF_2CF_2O)_nCF_2CF_2CF_2CH_2$—O—$CH_2CH(OH)CH_2OH$ (Compound 3)

The reaction was conducted in the same manner as in Example 1 except that a fluoropolyether of the formula HO—$CH_2CF_2CF_2CF_2O(CF_2CF_2CF_2CF_2O)_nCF_2CF_2CF_2$—$CH_2$—OH is used in place of the fluoropolyether of the formula HO—$CH_2CF_2O(CF_2CF_2O)_x(CF_2O)_y$—$CF_2CH_2$—OH used in Example 1, affording 63 g of Compound 3.

Compound 3 was a colorless transparent liquid and 1.72 g/cm³ in density at 20° C. Compound 3 was identified by NMR with the result shown.

$^{19}$F-NMR (solvent: none, reference material: $OCF_2CF_2CF_2CF_2O$ in the obtained product being taken as −125.8 ppm)
δ=−83.7 ppm [16F, —$OCF_2CF_2CF_2CF_2O$—, —$OCF_2CF_2CF_2CH_2OCH_2CH(OH)CH_2$—O—$C_6H_5$, —$OCF_2CF_2CF_2CH_2OCH_2CH(OH)CH_2OH$],
δ=−123.3 ppm [4F, —$OCF_2CF_2CF_2CH_2OCH_2CH(OH)CH_2$—O—$C_6H_5$, —$OCF_2CF_2CF_2CH_2OCH_2CH(OH)CH_2OH$],
δ=−125.8 ppm [12F, —$OCF_2CF_2CF_2CF_2O$—],
δ=−127.6 ppm [4F, —$OCF_2CF_2CH_2OCH_2CH(OH)CH_2$—$C_6H_5$, —$OCF_2CF_2CH_2OCH_2CH(OH)CH_2OH$]
n=3.0

$^1$H—NMR (solvent: none, reference material: $D_2O$)
δ=3.2~3.8 ppm 16H, $C_6H_5O$—$CH_2CH(OH)CH_2O$—$CH_2CF_2CF_2CF_2O$—$(CF_2CF_2CF_2CF_2O)_zCF_2CF_2CF_2CH_2$—O—$CH_2CH(OH)CH_2OH$]
δ=6.1 ppm, 6.7 ppm [5H, $OCF_2CH_2OCH_2CH(OH)CH_2$—$C_6H_5$]

Example 4

Preparation of CH$_3$O—C$_6$H$_4$O—CH$_2$CH(OH)
CH$_2$OCH$_2$—CF$_2$O(CF$_2$CF$_2$O)$_x$(CF$_2$O)$_y$CF$_2$—CH$_2$—
O—CH$_2$CH(OH)CH$_2$OH (Compound 4)

The reaction was conducted in the same manner as in Example 1 except that glycidyl 4-methoxyphenyl ether is used in place of glycidyl phenyl ether, affording 66 g of Compound 4.

Compound 4 was a colorless transparent liquid and 1.74 g/cm$^3$ in density at 20° C. Compound 4 was identified by NMR with the result shown.

$^{19}$F-NMR (solvent: none, reference material: OCF$_2$CF$_2$CF$_2$O in the obtained product being taken as −125.8 ppm)

δ=−52.1 ppm, −53.7 ppm, −55.4 ppm [12F, —OCF$_2$—],

δ=−89.1 ppm, −90.7 ppm [24F, —OC$\underline{F}_2$CF$_2$O—],

δ=−77.9 ppm, −80.0 ppm [4F, —OC$\underline{F}_2$CH$_2$OCH$_2$CH(OH)CH$_2$—O—C$_6$H$_4$—OCH$_3$, —OC$\underline{F}_2$CH$_2$OCH$_2$CH(OH)CH$_2$OH], x=6.1, y=6.4

$^1$H—NMR (solvent: none, reference material: D$_2$O)

δ=3.2~3.8 ppm [20H, CH$_3$O—C$_6$H$_4$O—C$\underline{H}_2$CH(OH)C$\underline{H}_2$OC$\underline{H}_2$CF$_2$O(CF$_2$CF$_2$O)$_x$(CF$_2$O)$_y$CF$_2$C$\underline{H}_2$—O—C$\underline{H}_2$C$\underline{H}$(OH)C$\underline{H}_2$OH]

δ=6.1 ppm, 6.7 ppm [4H, —OCF$_2$CH$_2$OCH$_2$CH(OH)CH$_2$—C$_6$$\underline{H}_4$—OCH$_3$]

Example 5

Preparation of CH$_3$O—C$_6$H$_4$O—CH$_2$CH(OH)
CH$_2$O—CH$_2$CF$_2$CF$_2$O(CF$_2$CF$_2$CF$_2$O)$_z$CF$_2$CF$_2$CH$_2$—O—CH$_2$CH(OH)CH$_2$OH
(Compound 5)

The reaction was conducted in the same manner as in Example 2 except that glycidyl 4-methoxyphenyl ether is used in place of glycidyl phenyl ether, affording 71 g of Compound 5.

Compound 5 was a colorless transparent liquid and 1.75 g/cm$^3$ in density at 20° C. Compound 5 was identified by NMR with the result shown.

$^{19}$F-NMR (solvent: none, reference material: OCF$_2$CF$_2$CF$_2$O in the obtained product being taken as −129.7 ppm)

δ=−129.7 ppm [12F, —OCF$_2$CF$_2$CF$_2$O—]

δ=−83.7 [24F, —OC$\underline{F}_2$CF$_2$CF$_2$O—],

δ=−124.2 ppm [4F, —OC$\underline{F}_2$CF$_2$CH$_2$OCH$_2$CH(OH)CH$_2$—O—C$_6$H$_4$—OCH$_3$, —OC$\underline{F}_2$CF$_2$CH$_2$OCH$_2$CH(OH)CH$_2$OH], δ=−86.5 ppm [4F, —OCF$_2$C$\underline{F}_2$CH$_2$OCH$_2$CH(OH)CH$_2$—O—C$_6$H$_4$—OCH$_3$, —OCF$_2$C$\underline{F}_2$CH$_2$OCH$_2$CH(OH)CH$_2$OH]

z=6.3

$^1$H—NMR (solvent: none, reference material: D$_2$O)

δ=3.2~3.8 ppm [20H, CH$_3$O—C$_6$H$_4$O—C$\underline{H}_2$CH(OH)C$\underline{H}_2$O—CH$_2$CF$_2$CF$_2$O(CF$_2$CF$_2$CF$_2$O)$_z$CF$_2$CF$_2$C$\underline{H}_2$—O—C$\underline{H}_2$CH(OH)CH$_2$OH]

δ=6.1 ppm, 6.7 ppm [4H, —OCF$_2$CF$_2$CH$_2$OCH$_2$CH(OH)CH$_2$—C$_6$$\underline{H}_4$—OCH$_3$]

Example 6

Preparation of CH$_3$O—C$_6$H$_4$O—CH$_2$CH(OH)
CH$_2$O—CH$_2$CF$_2$CF$_2$CF$_2$O—(CF$_2$CF$_2$CF$_2$CF$_2$O)$_n$CF$_2$CF$_2$CF$_2$CH$_2$—O—CH$_2$CH(OH)CH$_2$OH
(Compound 6)

The reaction was conducted in the same manner as in Example 3 except that glycidyl 4-methoxyphenyl ether is used in place of glycidyl phenyl ether, affording 59 g of Compound 6.

Compound 6 was a colorless transparent liquid and 1.75 g/cm$^3$ in density at 20° C. Compound 6 was identified by NMR with the result shown.

$^{19}$F-NMR (solvent: none, reference material: OCF$_2$CF$_2$CF$_2$CF$_2$O in the obtained product being taken as −125.8 ppm)

δ=−83.7 ppm [16F, —OCF$_2$CF$_2$CF$_2$CF$_2$O—, —OC$\underline{F}_2$CF$_2$CF$_2$CH$_2$OCH$_2$CH(OH)C$\underline{H}_2$—O—C$_6$H$_4$—OCH$_3$, —OC$\underline{F}_2$CF$_2$CF$_2$CH$_2$OCH$_2$CH(OH)CH$_2$OH], δ=−123.3 ppm [4F, —OCF$_2$C$\underline{F}_2$CF$_2$CH$_2$OCH$_2$CH(OH)CH$_2$—O—C$_6$H$_4$—OCH$_3$, —OC$\underline{F}_2$CF$_2$CF$_2$CH$_2$OCH$_2$CH(OH)CH$_2$OH], δ=−125.8 ppm [12F, —OCF$_2$CF$_2$CF$_2$CF$_2$O—], δ=−127.6 ppm [4F, —OCF$_2$CF$_2$C$\underline{F}_2$CH$_2$OCH$_2$CH(OH)CH$_2$—C$_6$H$_4$—OCH$_3$, —OCF$_2$C$\underline{F}_2$CF$_2$CH$_2$OCH$_2$CH(OH)CH$_2$OH]

n=3.0

$^1$H—NMR (solvent: none, reference material: D$_2$O)

δ=3.2~3.8 ppm [20H, CH$_3$O—C$_6$H$_4$O—C$\underline{H}_2$CH(OH)C$\underline{H}_2$O—C$\underline{H}_2$CF$_2$CF$_2$CF$_2$O(CF$_2$CF$_2$CF$_2$CF$_2$O)$_z$CF$_2$CF$_2$CF$_2$C$\underline{H}_2$—O—C$\underline{H}_2$CH(OH)CH$_2$OH]

δ=6.1 ppm, 6.7 ppm [4H, —OCF$_2$CH$_2$OCH$_2$CH(OH)CH$_2$—C$_6$$\underline{H}_4$—OCH$_3$]

Example 7

Preparation of C$_6$H$_5$O—CH$_2$CH(OH)CH$_2$OCH$_2$—
CF$_2$O(CF$_2$CF$_2$O)$_x$(CF$_2$O)$_y$CF$_2$—CH$_2$—O—
CH$_2$CH$_2$OH (Compound 7)

Ditrifluoromethylbenzene (180 g), 60 g of a fluoropolyether of the formula HO—CH$_2$CF$_2$O(CF$_2$CF$_2$O)$_x$(CF$_2$O)$_y$CF$_2$—CH$_2$—OH which is 1305 in number average molecular weight and 1.25 in molecular weight distribution, 2-bromoethanol (12 g) and metal sodium (4 g) were stirred at 60° C. in an argon atmosphere for 120 hours. The mixture was thereafter washed with water, dewatered and purified by silica gel chromatography, affording 30 g of perfluoropolyether (average molecular weight: 1310) having one hydroxyl group at one terminal and 2-hydroxyethyl group at the other terminal. This compound (30 g) was dissolved in a t-butanol (60 g), potassium t-butoxide (0.5 g) and glycidyl phenyl ether (15 g) were added to the solution, and the mixture was stirred at 70° C. for 17 hours. The mixture was thereafter washed with water, dewatered and purified by silica gel chromatography, affording 12 g of Compound 7.

Compound 7 was a colorless transparent liquid and 1.74 g/cm$^3$ in density at 20° C. Compound 7 was identified by NMR with the result shown.

$^{19}$F-NMR (solvent: none, reference material: OCF$_2$CF$_2$CF$_2$O in the obtained product being taken as −125.8 ppm)

δ=−52.1 ppm, −53.7 ppm, −55.4 ppm [12F, —OCF$_2$—],

δ=−89.1 ppm, −90.7 ppm [24F, —OC$\underline{F}_2$CF$_2$O—],

δ=−77.9 ppm, −80.0 ppm [4F, —OC$\underline{F}_2$CH$_2$OCH$_2$CH(OH)CH$_2$—O—C$_6$H$_5$, —C$\underline{F}_2$CH$_2$OCH$_2$CH$_2$OH]

x=6.1, y=6.4

$^1$H—NMR (solvent: none, reference material: D$_2$O)
δ=3.53~3.82 ppm [14H, C$_6$H$_5$O—CH$_2$CH(OH)CH$_2$OCH$_2$—CF$_2$O(CF$_2$CF$_2$O)$_x$(CF$_2$O)$_y$CF$_2$—CH$_2$—O—CF$_2$CH$_2$OCH$_2$CH$_2$OH],
δ=4.61 ppm [1H, —CF$_2$CH$_2$OCH$_2$CH$_2$OH],
δ=6.1 ppm, 6.7 ppm [5H, —OCF$_2$CH$_2$OCH$_2$CH(OH)CH$_2$—C$_6$H$_5$]

Example 8

Preparation of C$_6$H$_5$O—CH$_2$CH(OH)CH$_2$O—CH$_2$CF$_2$CF$_2$O(CF$_2$CF$_2$CF$_2$O)$_z$CF$_2$CF$_2$CH$_2$—O—CH$_2$CH$_2$OH (Compound 8)

The reaction was conducted in the same manner as in Example 7 except that a fluoropolyether of the formula HO—CH$_2$CF$_2$CF$_2$O(CF$_2$CF$_2$CF$_2$O)$_z$CF$_2$CF$_2$—CH$_2$—OH is used in place of the fluoropolyether of the formula HO—CH$_2$CF$_2$O(CF$_2$CF$_2$O)$_x$(CF$_2$O)$_y$—CF$_2$CH$_2$—OH used in Example 7, affording 15 g of Compound 8.

Compound 8 was a colorless transparent liquid and 1.67 g/cm$^3$ in density at 20° C. Compound 8 was identified by NMR with the result shown.

$^{19}$F-NMR (solvent: none, reference material: OCF$_2$CF$_2$CF$_2$O in the obtained product being taken as −129.7 ppm)
δ=−129.7 ppm [12F, —OCF$_2$CF$_2$CF$_2$O—],
δ=−83.7 [24F, —OCF$_2$CF$_2$O—],
δ=−124.2 ppm [4F, —OCF$_2$CF$_2$CH$_2$OCH$_2$CH(OH)CH$_2$—O—C$_6$H$_5$, —OCF$_2$CF$_2$CH$_2$OCH$_2$CH$_2$OH],
δ=−86.5 ppm [4F, —OCF$_2$CF$_2$CH$_2$OCH$_2$CH(OH)CH$_2$—O—C$_6$H$_5$, —OCF$_2$CF$_2$CH$_2$OCH$_2$CH$_2$OH],
z=6.3

$^1$H—NMR (solvent: none, reference material: D$_2$O)
δ=3.2~3.8 ppm [14H, C$_6$H$_5$O—CH$_2$CH(OH)CH$_2$O—CH$_2$CF$_2$CF$_2$O(CF$_2$CF$_2$CF$_2$O)$_z$CF$_2$CF$_2$CH$_2$—O—CH$_2$CH$_2$OH]
δ=4.61 ppm [1H, —CF$_2$CH$_2$OCH$_2$CH$_2$OH],
δ=6.1 ppm, 6.7 ppm [5H, —OCF$_2$CF$_2$CH$_2$OCH$_2$CH(OH)CH$_2$—C$_6$H$_5$]

Example 9

Preparation of C$_6$H$_5$O—CH$_2$CH(OH)CH$_2$O—CH$_2$CF$_2$CF$_2$CF$_2$O(CF$_2$CF$_2$CF$_2$CF$_2$O)$_n$CF$_2$CF$_2$CF$_2$CH$_2$—O—CH$_2$CH$_2$OH (Compound 9)

The reaction was conducted in the same manner as in Example 7 except that a fluoropolyether of the formula HO—CH$_2$CF$_2$CF$_2$CF$_2$O(CF$_2$CF$_2$CF$_2$CF$_2$O)$_n$CF$_2$CF$_2$CF$_2$—CH$_2$—OH is used in place of the fluoropolyether of the formula HO—CH$_2$CF$_2$O(CF$_2$CF$_2$O)$_x$(CF$_2$O)$_y$—CF$_2$CH$_2$—OH used in Example 7, affording 10 g of Compound 9.

Compound 9 was a colorless transparent liquid and 1.75 g/cm$^3$ in density at 20° C. Compound 9 was identified by NMR with the result shown.

$^{19}$F-NMR (solvent: none, reference material: OCF$_2$CF$_2$CF$_2$CF$_2$O in the obtained product being taken as −125.8 ppm)
δ=−83.7 ppm [16F, —OCF$_2$CF$_2$CF$_2$CF$_2$O—, —OCF$_2$CF$_2$CF$_2$CH$_2$OCH$_2$CH(OH)CH$_2$—O—C$_6$H$_5$, —OCF$_2$CF$_2$CF$_2$CH$_2$OCH$_2$CH$_2$OH],
δ=−123.3 ppm [4F, —OCF$_2$CF$_2$CF$_2$CH$_2$OCH$_2$CH(OH)CH$_2$—O—C$_6$H$_4$—OCH$_3$, —OCF$_2$CF$_2$CF$_2$CH$_2$OCH$_2$CH$_2$OH],
δ=−125.8 ppm [12F, —OCF$_2$CF$_2$CF$_2$CF$_2$O—],
δ=−127.6 ppm [4F, —OCF$_2$CF$_2$CH$_2$OCH$_2$CH(OH)CH$_2$—C$_6$H$_5$, —OCF$_2$CF$_2$CH$_2$OCH$_2$CH$_2$OH]
n=3.0

$^1$H—NMR (solvent: none, reference material: D$_2$O)
δ=3.2~3.8 ppm [14H, C$_6$H$_5$O—CH$_2$CH(OH)CH$_2$O—CH$_2$CF$_2$CF$_2$CF$_2$O(CF$_2$CF$_2$CF$_2$CF$_2$O)$_z$CF$_2$CF$_2$CF$_2$CH$_2$—O—CH$_2$CH$_2$OH],
δ=4.61 ppm [1H, —CF$_2$CH$_2$OCH$_2$CH$_2$OH],
δ=6.1 ppm, 6.7 ppm [5H, —OCF$_2$CH$_2$OCH$_2$CH(OH)CH$_2$—C$_6$H$_5$]

Example 10

Measurement of Decomposition Resistance to Aluminum Oxide

A sample was used for evaluation which was prepared from each of Compounds 1 and 2, by adding 20 wt. % of Al$_2$O$_3$ to the lubricant, intensely shaking the mixture and thereafter thoroughly agitating the mixture with ultrasonic waves. The sample was checked for decomposition resistance using a thermal analyzer (TG/TDA). The sample was heated at 250° C. for 100 minutes, and the weight reduction (B) of the lubricant was measured. For comparison, 20 mg of each of Compounds 1 and 2 was thermally analyzed in the same manner as above with the exception of adding no Al$_2$O$_3$ to obtain the weight reduction (C). Decomposition Resistance was evaluated by (B-C).

Example 11

Measurement of Mono-Layer Thickness

As disclosed in Nonpatent Literature 2, the lubricant applied to a magnetic disk can be checked for mono-layer thickness (thickness per molecule) when the diffusion behavior of the lubricant on the disk is observed by an ellipsometer. The mono-layer thickness is obtained as the thickness of a terrace portion of the lubricant film.

Nonpatent Literature 2: Journal of Tribology, Oct. , 2004, Vol. 126, p751

Stated more specifically, Compounds 1 and 2 prepared in Examples were respectively dissolved in portions of Vertrel-XF manufactured by DuPont. These solutions contain the respective Compounds 1 and 2 at a concentration of 0.05 wt. %. A portion (about ¼) of a magnetic disk, 2.5 inches in diameter, was dipped in each of the solutions and withdrawn at a rate of 4 mm/s to obtain a disk comprising a portion coated with one of Compounds 1 and 2 and an uncoated portion. The coated portions thus obtained were 20 angstroms in average thickness.

Each of the disks thus prepared was immediately attached to the ellipsometer and checked for variations in film thickness in the boundary between the coated portion and the uncoated portion at a specified time interval under the temperature condition of 50° C. to obtain the mono-layer thickness of the lubricant as the film thickness of the terrace portion to be provided.

Also used for comparison were Lubricant 10 having cyclophosphazene group, and Lubricant 11 having two hydroxyl groups each of molecular terminals.

(m-CF$_3$—C$_6$H$_4$O)$_5$(P$_3$N$_3$)OCH$_2$CF$_2$O(CF$_2$CF$_2$O)$_x$(CF$_2$O)$_y$CF$_2$CH$_2$OCH$_2$CH(OH)CH$_2$OH    (Lubricant 10)

wherein x is 10.1, y is 10.9, and 1.18 in molecular weight distribution.

HOCH$_2$CH(OH)CH$_2$O(CF$_2$CF$_2$O)$_x$(CF$_2$O)$_y$CH$_2$CH(OH)CH$_2$OH    (Lubricant 11)

wherein x is 9.8, y is 9.7, and 1.20 in molecular weight distribution.

Table 1 shows the evaluation of decomposition resistance and mono-layer thickness measurements. These results indicate that the perfluoropolyether compounds of the invention having an aromatic group and hydroxyl have relative decomposition resistance and a smaller mono-layer thickness than that of the perfluoropolyether compound having cyclophosphazene group.

TABLE 1

| Specimen | Decomposition Resistance to aluminum oxide (%) | Mono-layer thickness (Å) |
|---|---|---|
| Compound 1 | 10 | 10.1 |
| Compound 2 | 10 | 9.3 |
| Lubricant 10 | 10 | 17.3 |
| Lubricant 11 | 39 | 18.0 |

Example 12

Preparation of Magnetic Disk

Each of Compounds 1 and 2 obtained in examples was dissolved in Vertrel-XF, product of DuPont. The solution was 0.05 wt. % in the concentration of Compounds 1 and 2. A magnetic disk, 2.5 inches in diameter, was immersed in the solution for 1 minute and then withdrawn at a rate of 2 mm/s. The disk was thereafter dried at 150° C. for 10 minutes. The coated compound was thereafter checked by FT-IR for film thickness.

Table 2 shows the results. It was confirmed that the magnetic disk can be obtained which is coated with the present compound, and has higher decomposition resistance and a smaller mono-layer thickness.

TABLE 2

| Specimen | Film thickness (Å) |
|---|---|
| Compound 1 | 11 |
| Compound 2 | 11 |

EXPLANATION OF THE SYMBOL

1: substrate;
2: recording layer;
3: protective layer;
4: lubricant layer

The invention claimed is:

1. A compound of the formula (1)

(1)

wherein $R^1$ is hydrogen, alkoxyl having 1 to 4 carbon atoms, amino or amido, $R^2$ is —$CF_2O(CF_2CF_2O)_x(CF_2O)_yCF_2$—, —$CF_2CF_2O(CF_2CF_2CF_2O)_z$—$CF_2CF_2$— or —$CF_2CF_2CF_2O(CF_2CF_2CF_2CF_2O)_nCF_2CF_2CF_2$—, x and y are each an integer of 0 to 15, z is an integer of 1 to 15, n is an integer of 0 to 4, $R^3$ is —$CH_2CH(OH)CH_2OH$, —$CH_2CH(OH)CH_2OCH_2CH(OH)CH_2OH$ or —$(CH_2)_mOH$, m is an integer of 2 to 6.

2. A compound as defined in claim 1 wherein x and y are each a real number of 0 to 10, and z is a real number of 1 to 10.

3. A lubricant containing a compound of the formula (1)

(1)

wherein $R^1$ is hydrogen, alkoxyl having 1 to 4 carbon atoms, amino or amido, $R^2$ is —$CF_2O(CF_2CF_2O)_x(CF_2O)_yCF_2$—, —$CF_2CF_2O(CF_2CF_2CF_2O)_z$—$CF_2CF_2$— or —$CF_2CF_2CF_2O(CF_2CF_2CF_2CF_2O)_nCF_2CF_2CF_2$—, x and y are each an integer of 0 to 15, z is an integer of 1 to 15, n is an integer of 0 to 4, $R^3$ is —$CH_2CH(OH)CH_2OH$, —$CH_2CH(OH)CH_2OCH_2CH(OH)CH_2OH$ or —$(CH_2)_mOH$, m is an integer of 2 to 6.

4. A lubricant as defined in claim 3 wherein x and y are each a real number of 0 to 10, and z is a real number of 1 to 10.

5. A magnetic disk comprising at least a recording layer and a protective layer formed over a substrate, and a lubricating layer formed over the resulting surface, the lubricating layer containing a compound of the formula (1)

(1)

wherein $R^1$ is hydrogen, alkoxyl having 1 to 4 carbon atoms, amino or amido, $R^2$ is —$CF_2O(CF_2CF_2O)_x(CF_2O)_yCF_2$—, —$CF_2CF_2O(CF_2CF_2CF_2O)_z$—$CF_2CF_2$— or —$CF_2CF_2CF_2O(CF_2CF_2CF_2CF_2O)_nCF_2CF_2CF_2$—, x and y are each an integer of 0 to 15, z is an integer of 1 to 15, n is an integer of 0 to 4, $R^3$ is —$CH_2CH(OH)CH_2OH$, —$CH_2CH(OH)CH_2OCH_2CH(OH)CH_2OH$ or —$(CH_2)_mOH$, m is an integer of 2 to 6.

6. A magnetic disk as defined in claim 5 wherein x and y are each a real number of 0 to 10, and z is a real number of 1 to 10.

* * * * *